United States Patent [19]
Kupershmidt et al.

[11] Patent Number: 5,548,404
[45] Date of Patent: Aug. 20, 1996

[54] MULTIPLE WAVELENGTH POLARIZATION-MODULATED ELLIPSOMETER WITH PHASE-GENERATED CARRIER

[75] Inventors: Vladimir Kupershmidt, Pleasanton; Mikhail Kouchnir, Palo Alto; Robert Petersen, Dublin, all of Calif.

[73] Assignee: Sunshine Medical Instruments, Inc., Sausalito, Calif.

[21] Appl. No.: 311,263

[22] Filed: Sep. 23, 1994

[51] Int. Cl.$^6$ .................................................. G01J 4/00
[52] U.S. Cl. ............................................. 356/368; 356/369
[58] Field of Search ...................................... 356/364, 365, 356/366, 367, 368, 369; 250/225

[56] References Cited

U.S. PATENT DOCUMENTS

| | | |
|---|---|---|
| 4,176,951 | 12/1979 | Robert et al. . |
| 4,653,924 | 3/1987 | Itonaga et al. . |
| 4,901,728 | 2/1990 | Hutchison ............................... 356/368 |
| 4,983,823 | 1/1991 | Isobe . |
| 4,999,014 | 3/1991 | Gold et al. . |
| 5,018,863 | 5/1991 | Vareille et al. . |
| 5,034,617 | 7/1991 | Isobe . |
| 5,061,072 | 10/1991 | Folkard et al. . |
| 5,166,752 | 11/1992 | Spanier et al. . |
| 5,181,080 | 1/1993 | Fanton et al. . |
| 5,220,405 | 6/1993 | Barbee et al. . |
| 5,241,366 | 8/1993 | Bevis et al. . |
| 5,277,747 | 1/1994 | Aspnes . |
| 5,298,973 | 3/1994 | Fukazawa et al. . |
| 5,311,285 | 5/1994 | Oshige et al. . |

*Primary Examiner*—Richard A. Rosenberger
*Attorney, Agent, or Firm*—Orrick Herrington & Sutcliffe

[57] ABSTRACT

A method and apparatus for analyzing a sample wherein at least two orthogonally polarized, intensity and phase modulated laser beams with different wavelengths and frequencies of intensity and phase modulation are directed onto the sample, and the signals derived from the laser beams which interact with the sample are synchronously demodulated to determine characteristics of the sample such as index of refraction, absorption coefficient and film thickness. A reference beam can be provided to correct for noise and drift.

55 Claims, 6 Drawing Sheets

MULTIPLE WAVELENGTH POLARIZATION-MODULATED ELLIPSOMETER WITH PHASE-GENERATED CARRIER

FIELD OF THE INVENTION

The present invention relates to the non-destructive measurements of physical properties of samples, and, more particularly, to an ellipsometer employing at least two orthogonally polarized, intensity and phase modulated laser beams with different wavelengths and frequencies of modulation to analyze a sample, and synchronous demodulation of the detected signals.

BACKGROUND OF THE INVENTION

Ellipsometry is a nondestructive analysis technique for studying physical properties of samples based on changes in the polarization state of light caused by the interaction of a light beam with the sample. In all ellipsometer systems, a light beam having a known state of polarization is reflected off or transmitted through a sample. The difference between polarization states of the light beam before and after interaction with the sample can be used to calculate characteristics of the sample, such as film thickness, index of refraction, and absorption coefficients.

One common use for ellipsometry is the analysis of thin-film layers, such as a dielectric layer, on semiconductor samples. Reflection ellipsometry is presently considered to be the best method for measuring thicknesses of thin layers on semiconductors. While a number of parameters can be used to define a semiconductor sample with a coated dielectric layer, at least five parameters should be measured to completely characterize the sample: indexes of refraction of the film and substrate, absorption coefficients of the film and substrate, and the thickness of the film. For a given wavelength, however, ellipsometers allow measurement of only two parameters, $\psi$ and $\delta$, which relate to the magnitude of and phase shift between the S- and P-orthogonal polarization states of a beam reflected from a sample, respectively. If $R_P$ and $R_S$ are complex amplitude reflectivities of the polarized light reflected from the sample, then:

$$R_P/R_S = \tan \Psi \exp(i\delta)$$

Because only $\psi$ and $\delta$ can be measured, there is a so-called "order ambiguity," a classic problem with ellipsometry.

Another common problem with ellipsometry is that the measurement data is affected by intensity variation and background noise that ultimately set the limit on the accuracy and resolution of the instruments. Another problem, which prevents an ellipsometer from being used as a compact in-line instrument, is its inherent low-speed data collection rate. This data collection rate is particularly affected by time consuming alignment procedures and electronically controlled and mechanically rotating polarizer elements. The low speed of rotation of such polarizing elements sets an ultimate limit on the speed of data collection.

Electromechanical positioning problems due to vibration and difficulties in controlling and aligning rotating parts introduce further error into the test results. For example, the mechanically rotating polarizing elements have an inherent inaccuracy in its angular setting of about 0.05°. The phase difference between the rotating polarizing elements and the rotary encoder is also difficult to control.

Instead of rotating elements, some ellipsometers use a phase-modulation technique which utilizes electronically-controlled phase retardation. The signal-to-noise ratio is improved by eliminating the electromechanical elements. However, these ellipsometers cannot compensate for low-frequency drift which occurs in the phase modulation loop due to variations in the temperature and ambient conditions.

Photoelectric type modulation (PEM) ellipsometers, a type of phase modulation ellipsometer, present additional problems because they are resonance devices with a maximum excitation frequency between 70 and 100 kHz. The limited modulation range limits the capability of available demodulation techniques and also sets a limit on the speed of data collection.

SUMMARY OF THE INVENTION

To overcome these problems in the art, a method and apparatus for analyzing a sample is disclosed which directs at least two orthogonally polarized, optical frequency intensity and phase modulated laser beams with different wavelengths and frequencies of modulation, onto a surface and synchronously demodulates signals derived from the laser beams which interact with the surface. A reference beam is preferably provided to compensate for noise and drift.

A method of analyzing a sample is also disclosed comprising driving a first laser diode with a first modulated current to generate a first intensity modulated and optical frequency modulated laser beam having a first wavelength and driving a second laser diode with a second modulated current to generate a second intensity modulated and optical frequency modulated laser beam having a second wavelength. The laser beams are orthogonally polarized and subjected to different optical path lengths to introduce phase modulations at different frequencies of modulation. The phase modulated laser beams are directed onto a sample and the signals derived from the laser beams which interact with the sample are synchronously demodulated.

In another embodiment of the invention, a method of analyzing a thin film on a substrate comprises generating a first laser beam having a first wavelength intensity modulation and optical frequency modulation and generating a second laser beam having a second wavelength and optical frequency modulation intensity modulation, the first and second wavelengths and first and second frequencies being different. The first laser beam is polarized in a first direction and the second laser beam is polarized in a second direction perpendicular to the first direction. The phase of the first and second laser beams are modulated and the intensity and phase modulated laser beams are directed onto a sample. The signals derived from the laser beams which interact with the sample are then synchronously demodulated and analyzed to determine characteristics of the thin film.

In another embodiment of the invention, a method of analyzing a sample is disclosed comprising generating at least two intensity and optical frequency modulated laser beams each having different wavelengths and orthogonally polarizing each laser beam. The phase between the polarized components of each laser beam are modulated and the intensity and phase modulated laser beams are split into a reference beam and a probe beam. The reference beam is detected and the probe beam is directed onto a sample. The probe beam is detected after it interacts with the sample and the signals derived from the detected beams are synchronously demodulated. Characteristics of the sample are analyzed based on the demodulated signals.

An apparatus for analyzing surfaces is also disclosed comprising a first laser diode which emits a first intensity and optical frequency modulated laser beam at a first wavelength and a first frequency of modulation. A first polarizer located downstream of the first laser diode, the first polarizer polarizing the first laser beam in a first direction. A second laser diode is also provided which emits a second intensity modulated laser beam at a second wavelength and a second frequency of modulation. A second polarizer which polarizes the second laser beam in a second direction perpendicular to the first direction, is located downstream of the second laser diode. A birefringent polarization element is provided to introduce an optical path difference between perpendicular components of the polarized laser beams passing through it, such that the intensity modulated polarized laser beams become phase modulated. Coupler optics couples the polarized laser beams to the birefringent element. A photodetector is provided proximate the sample and a synchronous demodulator is operatively connected to the photodetector. An analyzer analyzes the demodulated signals to derive characteristics of the sample.

An ellipsometer is also disclosed comprising a first laser diode which emits a first laser beam at a first wavelength and a second laser diode which emits a second laser beam at a second wavelength. A current controller drives the first and second laser diodes with modulated current at first and second frequencies, respectively. A first polarizer is positioned downstream of the first laser diode having a first direction of polarization and a second polarizer is positioned downstream of the second laser diode having a second direction of polarization, the first and second directions of polarization being perpendicular to each other. A beam turning prism is located downstream of the first polarizer and a polarizing beam splitting cube is positioned downstream of the second polarizer. The prism and the cube are positioned such that the prism reflects the first laser beam through the cube and the cube reflects the second laser beam such that the first and second laser beams propagate in the same direction and coincide in space. A birefringent element is positioned downstream of the cube to introduce an optical path difference between the first and second directions of polarizations. A detector collects the laser beam output from the element which interacts with a sample. A synchronous demodulator demodulates the detected signals.

An apparatus for analyzing a surface is also disclosed comprising means for generating a first laser beam at a first wavelength of intensity modulation; means for generating a second laser beam at a second wavelength intensity modulation and optical frequency modulation; means for orthogonally polarizing the first and second laser beams; means for modulating the phase of the first and second means at different frequencies; means for coupling the orthogonally polarized laser beams to the means for modulating the phase; means for directing the intensity and phase modulated laser beams onto a sample; means for detecting laser beams which interact with the sample; means for synchronously demodulating signals derived from the detected laser beams; and means for analyzing the demodulated signals to derive characteristics of the sample.

In all the above embodiments, additional laser beams or laser diodes can be provided to analyze the sample.

BRIEF DESCRIPTION OF THE DRAWINGS

FIG. 5b is a top view of the BPE of FIG. 5a;

DETAILED DESCRIPTION OF THE INVENTION

Figure 1:
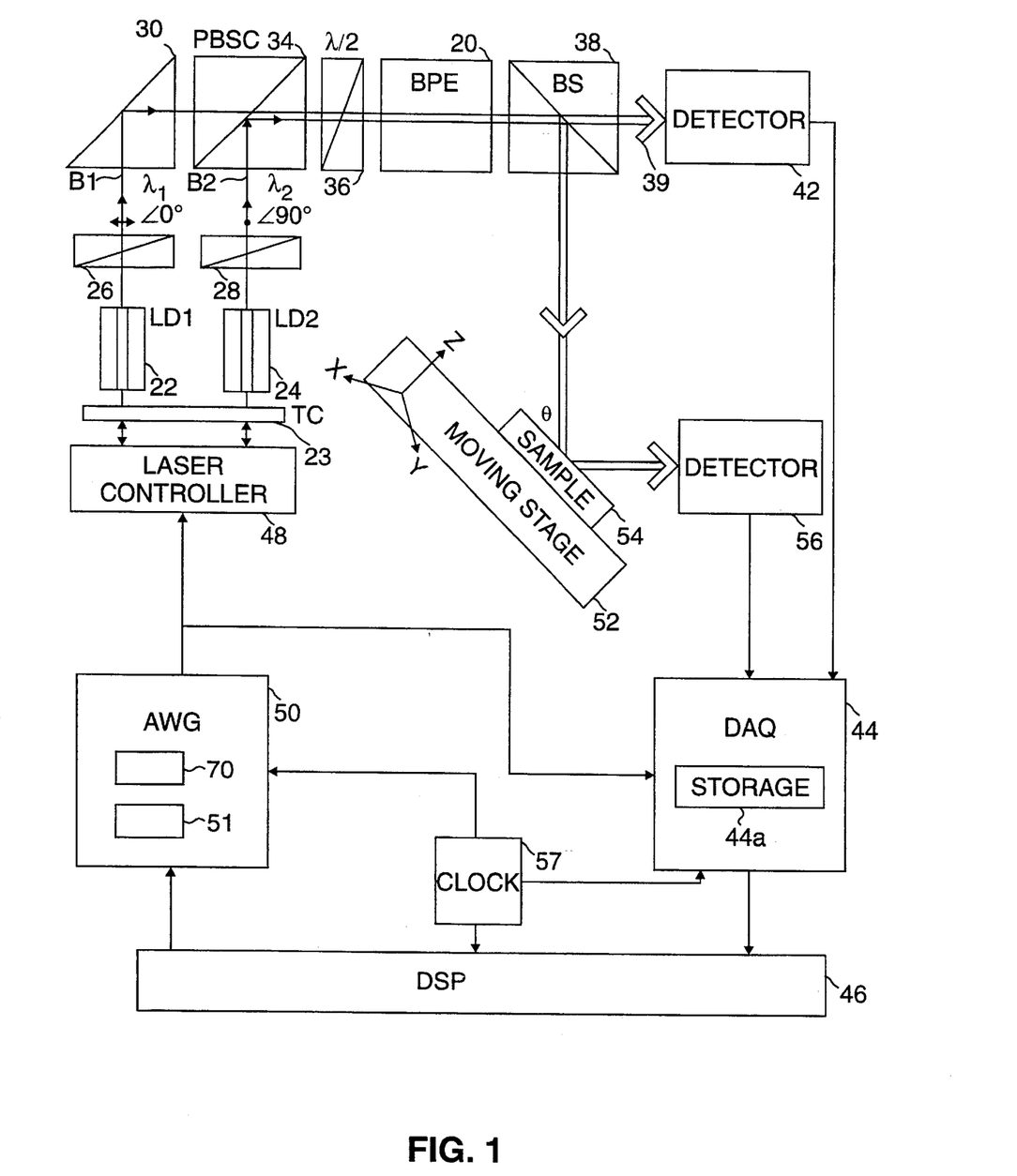
FIG. 1 is a block diagram of an ellipsometer in accordance with the present invention.

FIG. 1 is a block diagram of an ellipsometer 10 in accordance with the present invention. The ellipsometer 10 comprises a birefringent polarization element (BPE) 20 and at least two single-mode diode laser sources 22 and 24. The laser sources 22, 24 produce collimated laser beams B1 and B2 with different wavelengths λ1 and λ2, respectively, which are directed to the BPE 20 through a series of optical elements, described further below. The laser sources 22 and 24 preferably operate in the wavelength range of 680 to 1600 nanometers, simultaneously or in a time-sequence mode. The laser sources 22, 24 are preferably installed on a common thermocooler plate 23 for temperature equalization and stabilization.

A laser controller 48, which can be a current controller, drives the laser diodes 22, 24 with a bias current. Separate laser controllers can be provided for each laser diode as well. The laser controller 48 is driven by an arbitrary waveform generator (AWG) 50, which is preferably under the control of a digital signal processor (DSP) 46. A microprocessor can be used instead of the DSP 46, as well. The bias currents driving the laser diodes 22, 24 are modulated by different excitation currents generated by stimulus files 70 in the AWG 50, to modulate the intensity and frequency of the laser beams B1 and B2 output by the laser diodes 22 and 24 at different frequencies of modulation. The stimulus files 70 are preferably activated by trigger circuitry 51, which is activated by the DSP 46.

Polarizers 26 and 28, and coupling optics, such as a 90° beam-folding prism 30, and a polarizing beam-splitter cube (PBSC) 34, are preferably located between the laser diodes 22, 24, and the BPE 20. Other types of optical devices can be used to couple the output of the polarizers 26 and 28 to the BPE 20, as is known in the art.

The optical axes of the polarizers 26 and 28 are mutually perpendicular to each other so that one laser beam, beam B1, for example, is polarized in the P-direction and the other laser beam, beam B2, for example, is polarized in the S-direction, relative to the PBSC 34. After passing through the polarizer 26, the polarized beam B1 passes through the beam-folding prism 30, which reflects the laser beam B1 90° towards the PBSC 34. The PBSC 34 transmits the beam B1 without energy loss to the PBE 20. At the same time, the laser beam B2 produced by the laser source 24, and polarized by the polarizer 28 in the S-direction of polarization relative to the PBSC 34, is also reflected from the PBSC 34 without energy loss. At the output of PBSC 34, both beams B1 and B2 will have the same direction of propagation with mutually perpendicular P- and S-directions of polarization, respectively and will coincide in space.

A half-wave plate 36, which is located between the PBSC 34 and BPE 20 in FIG. 1, is arranged to rotate the direction of polarization of the beams B1 and B2 45° in the plane perpendicular to the direction of beam propagation. Therefore, when the beams B1 and B2 pass through the half-wave plate 36, their directions of polarization are still perpendicular to each other, and each beam will have P- and S-components.

The laser beams B1, B2 then pass through the BPE 20, which provides an optical path difference for light of different polarizations and wavelengths. Due to the optical path difference and the frequency modulation of the laser beams, the BPE 20 introduces a different phase shift to the P- and S-polarization components of each laser beam B1, B2.

At the output of the BPE 20, a beam splitter cube 38 is preferably provided to split each of the optical beams B1 and B2 into a reference optical beam 39 and a probe optical beam 40. The reference optical beam 39 is preferably provided to enable compensation for noise, drift, ambient light, or other system or environmental causes of inaccuracy. The probe beam 40 is used to analyze the sample. The reference beam 39 does not require high energy and can be a small portion, 2–7%, for example, of the energy of the probe beam 40. Other types of optical devices can be used to separate the reference beam 39 from the probe beam 40, as is known in the art. A photodetector 42 is preferably located after the BPE 20 in the direction of propagation to detect the reference beam 39. A preferred photodetector configuration is described further, below.

The ellipsometer 10 also includes a sample stage 52, which supports the sample 54 to be measured. The stage is oriented so that the laser beams are incident on the sample at a particular angle, dependent on the material being analyzed, as is known in the art. The stage 52 can preferably move along the perpendicular axes x, y and z in FIG. 1. A second photodetector 56 collects the laser beams reflected or transmitted from the sample 54 and converts them into electrical signals.

Each photodetector 42 and 56 is connected to a data acquisition system (DAQ) 44, which is in turn connected to the DSP 46. The AWG 50 also preferably supplies a signal to the DAQ 44 so that the AWG output can be monitored. The DAQ 44 converts analog signals received from the detectors 42, 56, to digital signals, which are provided to the DSP 46. The DSP 46 acts as a synchronous demodulator that demodulates and analyzes signals received from the photodetectors 42, 56, by one or a variety of techniques, as discussed further below. A microprocessor or central processing unit can be provided instead of the DSP 46.

The DSP 46, DAQ 44, and AWG 50 are preferably connected to the single clock source 57. Use of a single master clock to control the timing of the operation of each of these elements improves the synchronization of the system. Asynchronization has been found to be a significant source of error in ellipsometers. The DAQ 44, DSP 46 and AWG 50 are described further, below.

Figure 2:
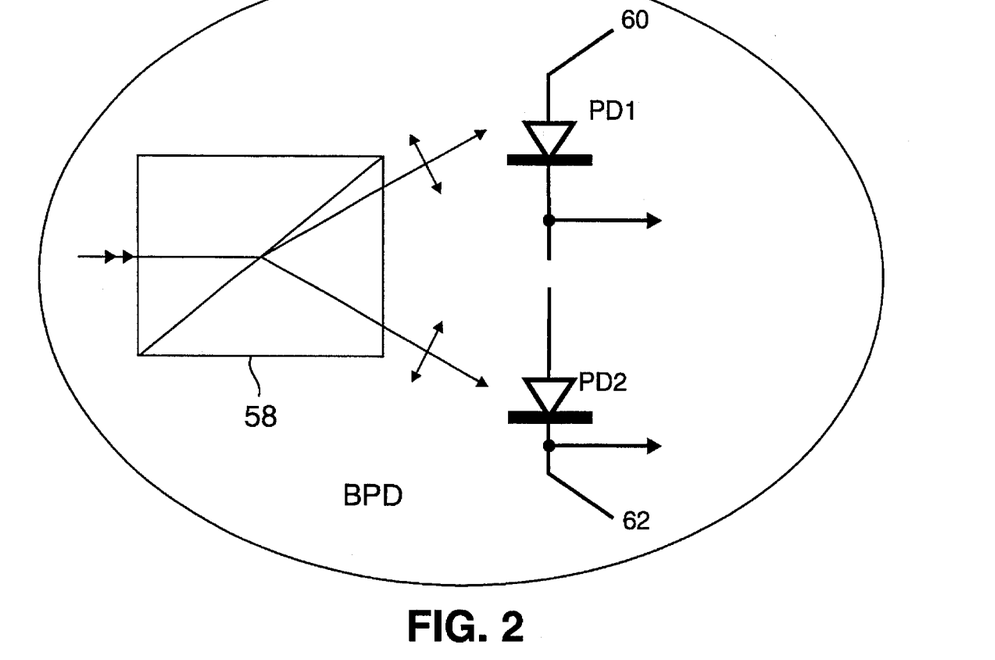
FIG. 2 is a schematic representation of a preferred balanced detector for use in the ellipsometer of FIG. 1.

The photodectors 42 and 56 are preferably balanced photodetectors. A preferred arrangement for either or both photodetectors 42 and 56 is shown in FIG. 2. A Wollaston prism 58 and two photodiodes 60 and 62 are provided. The Wollaston prism 58 splits an incident laser beam reflected from the sample 54 into two orthogonally polarized beams with respective angles χ equal to +45° and −45°. A polarized beam splitter cube, or some other means for splitting the laser beam into two orthogonally polarized beams separated in space, can be used instead of the prism. The outputs of each photodiode 60, 62 are provided directly to the DAQ 44. The outputs of each photodiode 60, 62 can also be provided to a differential amplifier (not shown), which provides the difference between the detected signals to the DAQ 44. Preferably, a gain stage is provided to the difference. The photodetectors PD1 and PD2 provide dual channel synchronous detection of the polarized beams, which improves the accuracy of measurements and cancels common optical noise in the system, as described further, below.

Figure 3A:
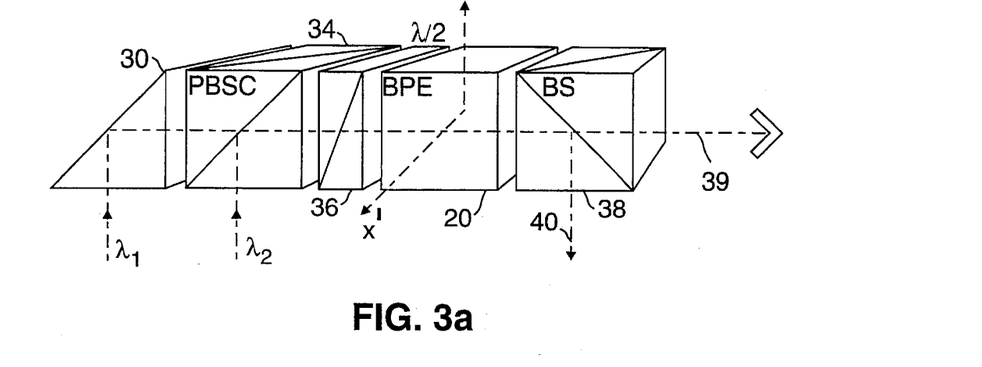
FIGS. 3a–3c are perspective views of three alternative embodiments of coupler optics for use in the ellipsometer of FIG. 1.
Figure 3B:
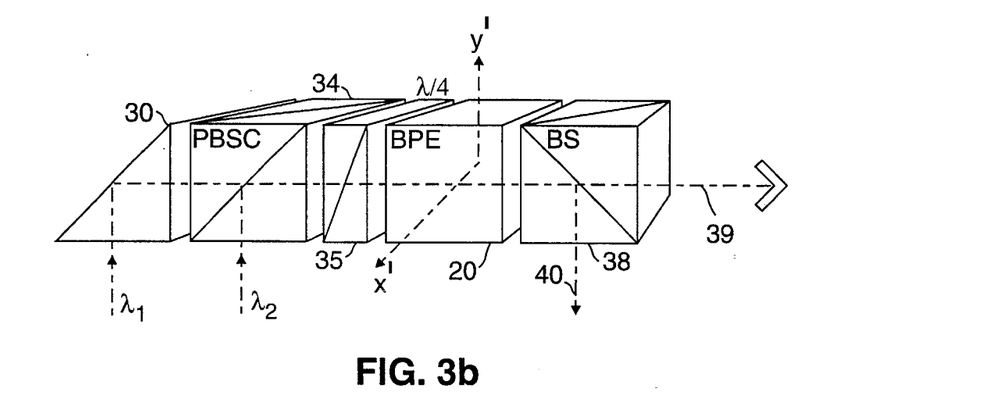
Figure 3C:
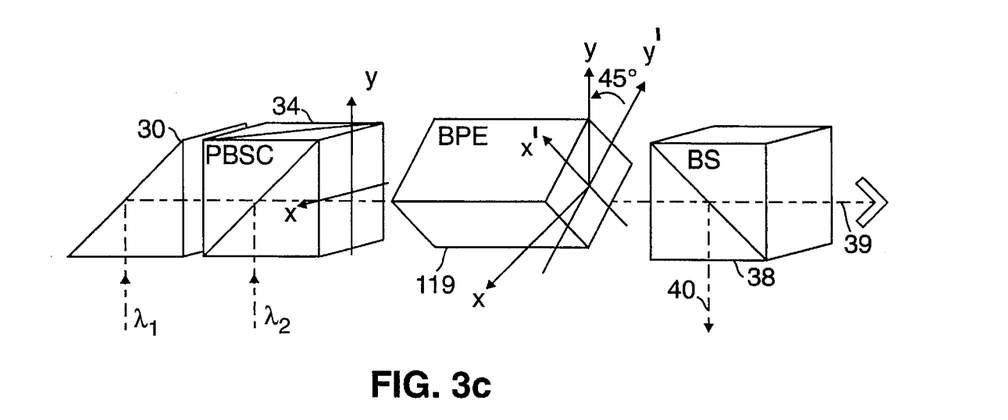

FIGS. 3a–3c are perspective views of three embodiments of the coupling optics of the ellipsometer of FIG. 1. The embodiment of FIG. 3a includes a half-wave plate 36, as shown in FIG. 1. The embodiment of FIG. 3b includes a quarter-wave plate 35 instead of the half-wave plate 36. The embodiment of FIG. 3c has a BPE 19 with optical axes X' and Y' oriented at 45° with respect to the optical axes X and Y of PBSC 34, instead of the wave plates.

The interaction of the laser beams with the BPE 20 will now be described. Since the beams B1 and B2 interact with the BPE 20 identically, only the passage of B1 will be referred to.

As discussed above, the BPE 20 produces a phase shift $\Delta\Phi_\lambda$ between the P- and S-polarized components of the beam B1 defined by:

$$\Delta\Phi_\lambda(t) = \frac{2\pi v(t)}{c} (L_P N_P - L_S N_S) \qquad (1)$$

where:

$L_P$ and $L_S$ are the geometrical-path lengths in the BPE travelled by the P- and S-components of beam B1 in the BPE, respectively;

$N_P$ and $N_S$ are indexes of refraction for the P- and S-components, respectively;

c is the speed of light, and v(t) is an instantaneous optical frequency of the laser beam B1.

In the presence of current modulation, the instantaneous optical frequency v(t) of the laser beam B1 can be expressed by the following formula:

$$v(t) = v_o(I) + \beta_\lambda I(t) \qquad (2)$$

where $v_o(I)$ is an optical frequency of the laser beam in the absence of current modulation, $\beta_\lambda$ is the modulation index of the laser diode, and I(t) is a waveform of current modulation output by the AWG 50.

Substituting Equation (2) into Equation (1), yields:

$$\Delta\Phi_\lambda(t) = \Delta\Phi_{0\lambda} + \frac{2\pi\beta_\lambda}{C} I(t)(L_P N_P - L_S N_S) \qquad (3)$$

where $\Delta\Phi_{0\lambda}$ is a phase shift corresponding to the frequency of $v_o(I)$, and is equal to $2\pi v_o(I)(L_P L_P - L_S L_S)/C$.

It can be seen from Equation (3) that by using the BPE 20 in combination with a laser diode driven by current modulation, it is possible to modulate the phase of the polarization components of the laser beam B1 by generation of a phase generated carrier. The electric field of the laser beam B1, which is a sum of the phase modulated P- and S-components, can be expressed in the following form:

$$\vec{E} = E_o(\vec{e}_P \exp(i\Delta\Phi_\lambda(t)) + \vec{e}_S) \quad (4)$$

where $E_o$ is an amplitude of the laser beam caused by current modulation, and $\vec{e}_P$ and $\vec{e}_S$ are single vectors of the P- and S-directions of polarization. The time dependence of the magnitudes of $E_o(t)$ and $\Delta\Phi_\lambda(t)$ are determined by the known waveform of current modulation.

The same result can be obtained using the quarter-wave plate 35 in FIG. 3b instead of half-wave plate 36 (FIG. 3a). In this case, the quarter-wave plate 35 converts the laser beams B1 and B2 into right- and left-hand circular polarized light beams which will interact with the BPE 20 in the same manner as described with respect to the system shown in FIG. 3a.

Generally, the electric field can be expressed as:

$$\vec{E} = E_o(t)(\vec{e}_P \exp(i\Delta\Phi_\lambda(t)) + \epsilon \vec{e}_S) \quad (5)$$

where $\epsilon=1$ for a $\lambda/2$ plate and $\epsilon=i$ for a $\lambda/4$ plate, $E_o(t)$ is an amplitude of the intensity of the laser beam caused by the current modulation, and $\vec{e}_P$ and $\vec{e}_S$ are single vectors of the P- and S-directions of polarization. The time dependence of the magnitudes of $E_o(t)$ and $\Delta\Phi_\lambda(t)$ are dependent upon the known waveform of current modulation.

Rotation of the polarization components can be achieved without the use of a waveplate by rotating the BPE 20 45° with respect to the optical axes X and Y of the PBSC, as shown in FIG. 3c. In this case, $\epsilon=1$ in Equation (5).

If an electromagnetic wave expressed by Equation (5) is directed onto the sample 54 at an incident angle $\theta$, the reflected or transmitted electromagnetic wave will have the following form:

$$\vec{E}_{Refl} = E_o(t)(|R_P|\vec{e}_P \exp(i\Delta\Phi_\lambda(t)+i\delta_P) + \epsilon|R_S|\vec{e}_S e^{i\delta_S}) \quad (6)$$

where $|R_P|$ and $|R_S|$ are the magnitudes of reflection for the P- and S-components, respectively, and $\delta_P$ and $\delta_S$ are the respective phase shifts, which are dependent in part on the incident angle $\theta$.

If an electromagnetic wave in the form of Equation (6) passes though a polarizing element, such as the Wollaston prism 58 of the preferred photodetector of FIG. 2, the element will produce a coherent mixture of P- and S-polarized components which contribute to the intensity of an AC signal $I_{AC}(t)$ generated at the output of a photodetector 56 of the form:

$$I_{AC}(t) = I_o(t)(|R_P|^2\cos^2\chi + |R_S|^2\sin^2\chi) + \\ I_o(t)|R_P R_S|\sin2\chi \begin{cases} \cos(\Delta\Phi_\lambda(t)+\delta) & \epsilon=1 \\ \sin(\Delta\Phi_\lambda(t)+\delta) & \epsilon=i \end{cases} \quad (7)$$

where $\chi$ is an angle between the optical axis of the polarizer and the P-direction of polarization, and $\delta$ is the phase difference between the P- and S-components ($\delta_P - \delta_S$).

Figure 4:
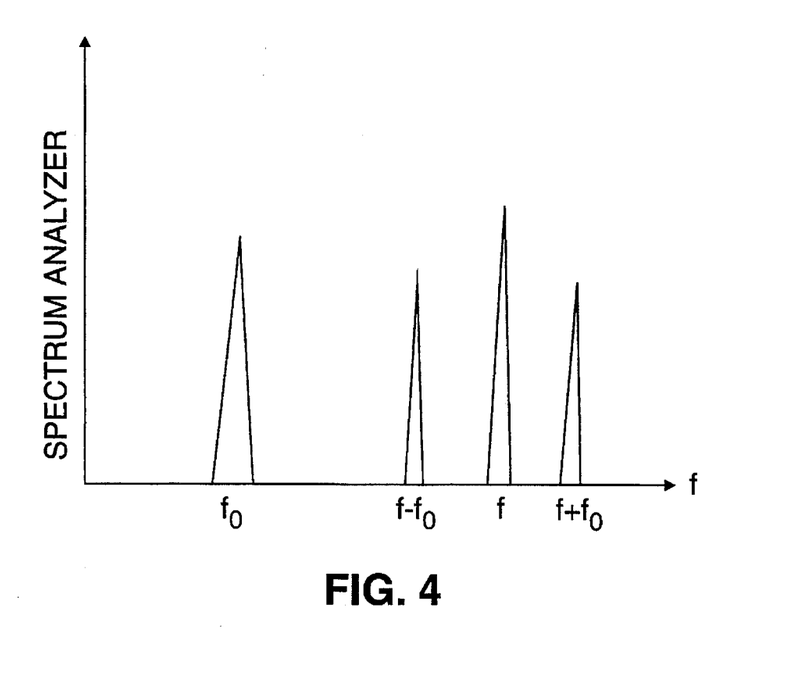
FIG. 4 is a graph of the amplitudes of signals derived from the ellipsometer of FIG. 1.

If the balanced photodetector of FIG. 2 is used, the sum $I_\Sigma(t)$ and difference $I_\Delta(t)$ of the $I_{AC}(t)$ signals corresponding to the angles $\chi$ of +45° and −45° can be expressed as follows:

$$I_\Sigma(t) = I_o(t)(|R_P|^2 + |R_S|^2) \quad (8a)$$

$$I_\Delta(t) = 2I_o(t)|R_P R_S| \cos(\Delta\Phi_\lambda(t)+\delta) \quad (8b)$$

where $I_o(t)$ is the intensity modulation of the laser beam B1 with frequency of current modulation $f_o$. $\Delta\Phi_\lambda(t)$, defined by Equation (3), has a frequency of phase modulation of f. In the frequency domain, the amplitudes of the sum $I_\Sigma(t)$ and difference $I\Delta(t)$ signals can be represented as shown in FIG. 4.

By using two-channel synchronous detection at a frequency of the current modulation $f_o$ and at the frequency of the phase modulation f, one can directly measure the amplitudes of the fundamental harmonics and the amplitude and phase of the phase generated carrier harmonics. In particular, the phase shift $\delta$ at frequency f represents the phase difference between the P- and S-polarized components of the laser beam B1 which interacts with the sample 54, expressed in Equation 8(b). A ratio of the amplitudes of the harmonics corresponding to the frequency of phase modulation f and the frequency of current modulation $f_o$ represent the contribution of the ellipsometer parameter $\psi$, as indicated below:

$$I_\Delta/I_\Sigma \sim \sin 2\Psi \quad (9)$$

There are several ways to synchronously demodulate the measured signals to determine the amplitude and phase shift caused by the interaction of the laser beams B1 with the sample 54. For example, the signal derived from the reference beam 39 (reference signal) by the detector 42 and the signal derived from the probe beam 40 after interaction with the sample (sample signal) by the detector 56 can each be compared to the signal output by the AWG 50. Comparison of the resultant values yields the phase shift in the probe beam 58 caused by the probe beam's interaction with the sample, corrected for noise and drift.

It is preferred to determine the in-phase (I) and quadrature (Q) components of the current and phase modulation frequencies of each of the detected signals by multiplying the reference signal and the sample signal by the sine and cosine of the fundamental or harmonic of the theoretical AWG 50 signal, and comparing those values to each other. The amplitude can be determined directly from I or Q.

Alternatively, if ramp modulation is used, the I and Q of the phase modulation can be determined by demodulating the sample signal with the reference signal. For example, the sample signal can be multiplied by the reference signal to obtain I. The sample signal can then be multiplied by the reference signal shifted 90° to obtain Q. This technique may provide better noise and drift compensation than the first technique, yielding more accurate results. The signal analysis may be more complex, however.

The phase difference can now be determined by differentiating and cross multiplying (DCM) the I and Q components of the detected sample and reference signals. While this technique is only applicable where the phase shift is not constant, a constant phase shift, as in the present invention, can be made non-constant by introduction of an AC dithering signal, as is known in the art.

The signals can also be analyzed by direct digital demodulation (DDM) which increases accuracy by time averaging. A dual lock-in amplifier difference technique, implemented in hardware or software, can also be used, wherein the signals at each detector 42, 56, are measured by a lock-in amplifier. The difference between the measurements is dependent on the phase shift caused by the interaction with the sample.

While any one of the above (or other) demodulation techniques may be used, it is preferable to use several to provide n-modular redundancy to increase the fault tolerance of the system.

The same measurements are preferably carried out for laser beam B2. If the index of refraction and absorption coefficient of a substrate are known, the use of the second laser diode enables the determination of the index of refraction, absorption coefficient and thickness of a film on the substrate. If the index of refraction and absorption coefficients of the substrate are not known, use of a third laser diode to generate a polarized laser beam at a third wavelength, orthogonally polarized with respect to the first two laser beams and with a different frequency of intensity and phase modulation, enables a complete characterization of the properties of the film and substrate. Additional laser diodes can be provided for improved characterization of the film and substrate. Additional PBSC's can be provided as part of the coupling optics, to accommodate the additional laser diodes. Operation of such laser diodes can be simultaneous, sequential or a combination thereof.

Since variations in intensity and ambient light effect $I_\Delta$ and $I_\Sigma$ equally, deviations caused by these factors, which can effect the intensity and to a lesser degree the phase shift of the measurements, cancel when taking the ratio of $I_\Delta$ and $I_\Sigma$.

Other potential sources of error which can cause deviations in the measured phase shift caused by interaction with the sample include the variation in the modulation index $\beta_\lambda$ of the laser diodes due to temperature fluctuations and frequency jitter of the laser beams (see Equation (2), above). Comparison of the reference beams 39 collected by the detector 42 to the sample beams collected at detector 56, as discussed above, enables correction for thermal fluctuation and frequency jitter, as well.

Another way to compensate for noise and drift is to compare the detected reference signal to an expected reference signal. The difference can then be used to adjust the measurement values during signal analysis. Since it takes a finite amount of time to calculate the difference, the adjustment should be made to the measurement signal taken at the appropriate time. While that difference can also be used in a feedback loop to adjust the waveform generated by the AWG 50 to drive the laser controller 48, as is known in the art, such a procedure can be slow.

Figure 5A:
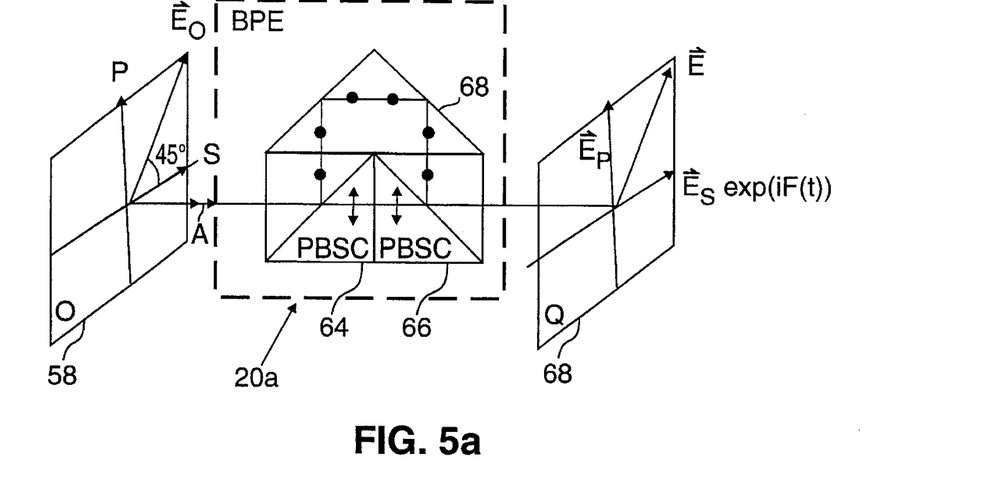
FIG. 5a is a partial perspective view of one embodiment of a birefringement polarization element (BPE) for use in the ellipsometer of FIG. 1.
Figure 5B:
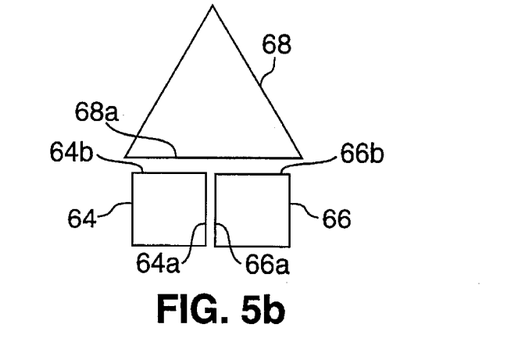

Depending on the specific application and design of the BPE 20, the laser controller 48 can generate a ramp or sine current modulation waveform to drive the laser diodes 22, 24. An embodiment of the BPE 20 having a Mach-Zehnder configuration used with a ramp current modulation waveform, for example, is shown in FIGS. 5a and 5b. Here, the BPE 20 consists of a PBSC 64, a PBSC 66, and a 90° total internal reflection prism 68, all preferably made of the same optical material. The PBSC 64 and PBSC 66 have main diagonal planes oriented perpendicular to each other. Sides 64a and 66a of the PBSC 64 and PBSC 66, respectively, are arranged parallel to each other and to output side of the PBSC 34 of FIG. 1. The base 68a of the prism 68 is oriented adjacent to surfaces 64b and 64c of the PBSC 64 and PBSC 66, respectively.

Shown on the left and right sides of the BPE 20 in FIG. 5a are input and output planes O and Q, respectively, perpendicular to the direction of propagation of the laser beam B1 indicated by the arrow A. The input plane O represents an output plane of polarization of the half-wave plate 36 of FIG. 1. The direction of polarization $\vec{E}_o$ of the input beam, and the direction of polarization of the output beam $\vec{E}_P$, are indicated as well.

The input direction of polarization $E_o$ is oriented 45° with respect to the polarization axis of the PBSC 34 (See FIG. 1). In FIG. 5a, the direction of the P-component is shown by vertical arrows, and the S-component direction is shown by black dots, indicating a direction perpendicular to the plane of the drawing. The P-polarized component of the laser beam B1 passes through the BPE 20 without energy loss, while the S-polarized component follows the path shown by the dots, also without energy loss. As a result, both polarized components of the laser beam B1 exit the BPE 20 along the same optical axis, but with a phase shift $\Delta\Phi_\lambda$ determined from Equation (1). In this case, the expression in parenthesis of Equation (1) will be equal to:

$$N(\lambda)(L_P - L_S) \tag{10}$$

where $N(\lambda)$ is the index of refraction of the optical material, and $(L_P - L_S)$ is a geometrical path length difference between P- and S-polarized components of the laser beam B1.

With the configuration of FIG. 5a and ramp current modulation, I(t) can be described as:

$$I(t) = I_o f_o t \tag{11}$$

where $I_o$ is an amplitude of current modulation and $f_o$ is the frequency of current modulation.

By substituting Equation (9) into Equation (3) and taking into account Equations (8a) and (8b), one can obtain the phase modulation of the polarized components of the laser beam in the following form:

$$\Delta\Phi_\lambda(t) = \Delta\Phi_{o\lambda} + 2\pi f t \tag{12}$$

where $f$ is a frequency of phase modulation (of the phase-generated carrier) and is equal to:

$$f = \frac{\beta_\lambda I_0 N_\lambda}{C} (L_P - L_S) f_0 \tag{13}$$

To avoid the spread of the frequency spectrum and to increase the accuracy and resolution of phase detection, the number of sine oscillations $f/f_o$ should be sufficiently high and represented by an integer.

The amplitude of current modulation of the laser diodes required in the present invention is dependent on the wavelength of the laser beam and the characteristics of the BPE 20. For example, Table A, below, shows the preferred depths of current modulation d ($d = I_o/I_{th}$, where $I_{th}$ is a threshold current of the laser diode), for a BPE 20a (FIG. 5a) for two types of optical materials: rutile and calcite, where the laser diode has an index of modulation $\beta_\lambda = 2$ GHz/mA, the PBSC 64 and PBSC 66 have sides equal to 10 mm and the prism 68 has sides equal to 12.7 mm. The laser diode can be a SDL-5400 produced by Spectra Diode Labs, Inc., San Jose, Calif., for example.

TABLE A

| Wavelength | Rutile (TiO$_2$) | Calcite |
| --- | --- | --- |
| $\lambda$ = 850 nm | d = 16% | d = 24% |
| $\lambda$ = 1300 nm | d = 16.2% | d = 24.2% |

Figure 6:
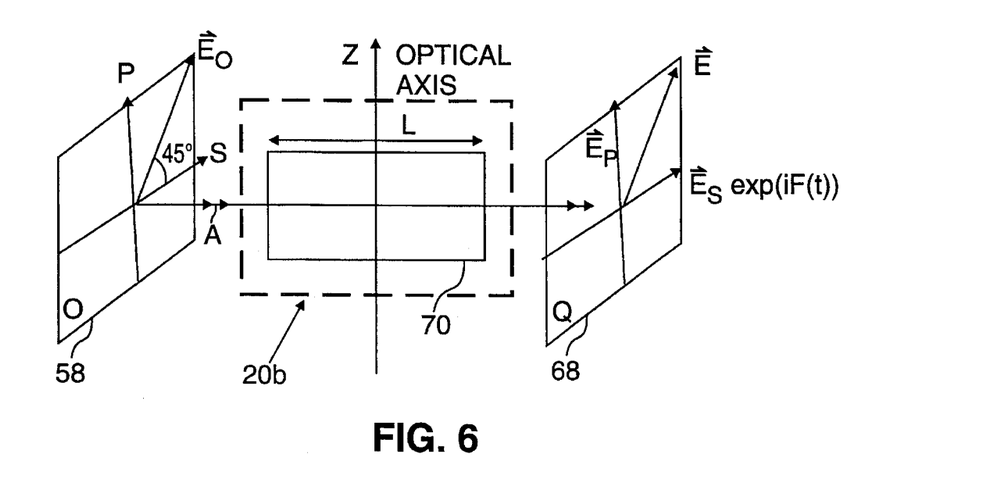
FIG. 6 is a schematic representation of another embodiment of a BPE.

A second embodiment of the BPE 20 is shown in FIG. 6. The BPE 20b consists of a single highly-birefringent optical element 70 with an optical length L and an optical axis Z which is oriented perpendicular to the direction of propagation of the laser beam B1. Shown on the left and right sides of the element 70 are the same input and output planes O and Q, respectively, that are shown in FIG. 5.

In this embodiment, the optical path length difference between the P- and S-components of the polarized beam B1 can be written as follows:

$$L_P N_P - L_S N_S = L(N_P - N_S) \tag{14}$$

The polarization-phase modulation $\Delta\Phi(t)$ which is determined from Equation (3) with reference to Equation (14)

will be carried out in conjunction with sine current modulation. In this case, the waveform of the phase-generated carrier (polarization-phase modulation) will also be represented in the sine waveform:

$$\Delta\Phi_\lambda(t) = \Delta\Phi_{o\lambda} + \Phi_{o\lambda} \sin 2\pi f t \qquad (15)$$

where $\Phi_{o\lambda}$ is an amplitude of polarization-phase modulation, which is equal to:

$$\Delta\Phi_{o\lambda} = 2\pi\beta_\lambda I_o L/c(N_P - N_S) \qquad (16)$$

The sine modulation is believed to be most effective when the amplitude of the phase modulation $\Phi_\lambda(t)$ is equal to about 2.405.

Figure 7:
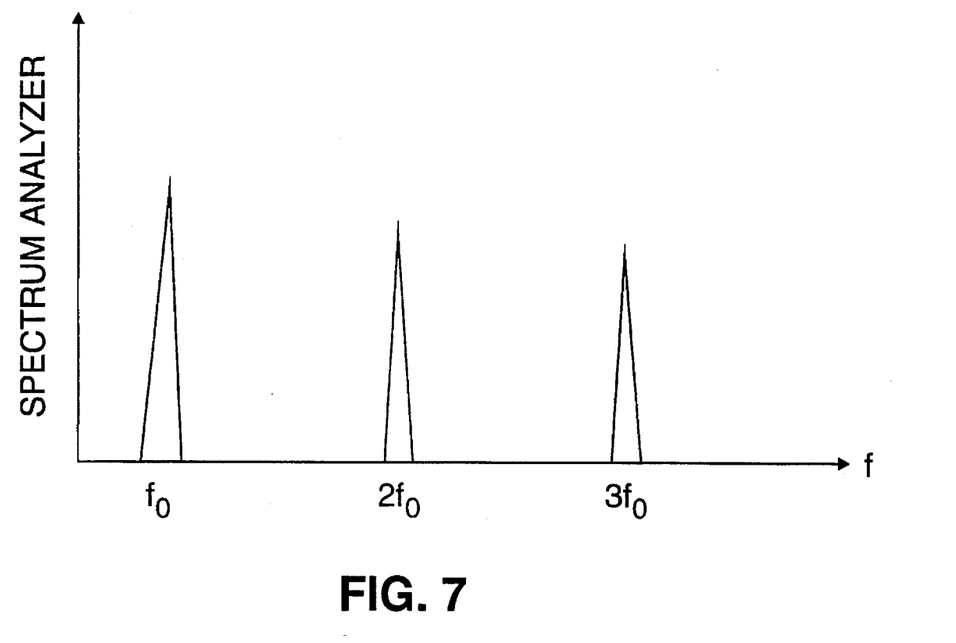
FIG. 7 is a graph of the even and odd harmonics of signals derived from the use of sine modulation with the ellipsometer of FIG. 1.

By substituting Equation (15) into Equations (7), (8a) and (8b), one can see that for sine modulation, the waveform measurement signals $I_\Sigma$ and $I_\Delta$ can be expressed in the form of a sum of odd and even harmonics at the modulation frequency $f_o$ as shown in FIG. 7.

One of the advantages of using ramp modulation is that the waveform of the phase-generated carrier (the phase modulation of the polarized components) is represented by a pure sine waveform, and hence a less sophisticated technique is required for signal demodulation, as is known in the art. For example, with ramp modulation, the detected signal for each laser beam needs to be demodulated at the frequency of intensity modulation and the frequency of phase modulation. With sine modulation, the detected signal of each laser beam must be demodulated at the frequency of intensity modulation, and at the frequencies of the second and third harmonics of the phase modulations. While more complex, the use of the sine wave modulation provides increased resolution and is therefore preferred to analyze films of less than about 500 Angstroms.

With the BPE 20b, where L=50.8, the preferred depth of current modulation d for the same laser diode described above, can be determined from Table B, below, for rutile or calcite.

TABLE B

| Wavelength | Rutile (TiO$_2$) | Calcite |
| --- | --- | --- |
| $\lambda$ = 850 nm | d = 5.8% | d = 9.2% |
| $\lambda$ = 1300 nm | d = 6% | d = 9.5% |

Figure 8:
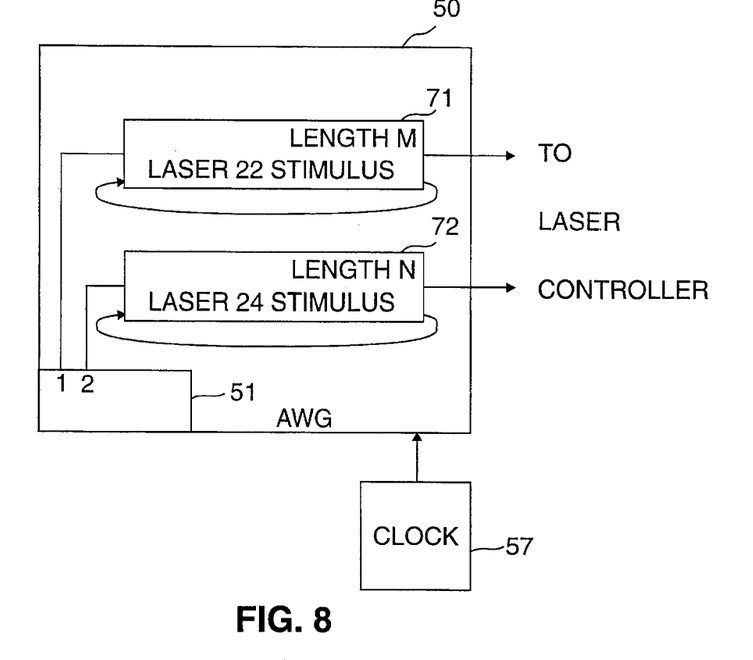
FIG. 8 is a block diagram of an example of an arbitrary waveform (AWG) generator for use in the ellipsometer of FIG. 1.

FIG. 8 illustrates the interaction between the AWG 50 and the laser controller 48. The AWG 50 preferably has multiple output channels, one for each laser. As mentioned above, operation of each channel can be separately controlled by data files, referred to as stimulus files 70, as shown in FIG. 1. The stimulus files are digitized representations of the desired analog signal to be output by the AWG 50 during run time. These stimulus files are mapped to the desired response of the individual laser diodes 22, 24. The desired response of these stimulus files are used as a part of an algorithm which operates the system.

A stimulus file 71 for the laser diode 22 with a length M and a stimulus file 72 for the laser diode 24 with a length N are shown in FIG. 8. The stimulus files 71 and 72 are activated via the trigger circuitry 51, such as trigger 1 and trigger 2, respectively, which are turned on by the DSP 46 at the appropriate time. The arrows in FIG. 8 indicate that the AWG 50 is operating continuously. The file lengths of the various stimulus files are preferably different for each laser source which operates at different modulation frequencies with non-overlapping harmonics.

In a purely theoretical solution, these stimulus files would generally be standard wave forms, such as sine waves or ramps. The actual response of the laser diodes to standard waveforms rarely matches the desired output, however. Non-linear characteristics of current-to-frequency conversion, for example, cause deviations in the output of the laser diode. Imperfections in individual lasers cause deviations, as well. These deviations are minimized and/or eliminated by compensating the stimulus file to produce the desired response of the laser diode during run time. This compensation is based on the calculated, statistical, and/or empirically derived behavior of the actual laser diode. Based on the desired output of the laser diode, a theoretical signal is first derived which would achieve that output in an ideal laser. Then, the theoretical signal is adjusted to compensate for known distortions which can change the output. Preferably, the actual output with the desired signal is compared to the desired output and further adjustments are made to the signal to achieve a better match. This signal is stored in the stimulus file and is output by the AWG 50 to drive the laser controller 48 and laser diodes 22, 24. Depending on the temporal characteristics of the resultant mapping, the stimulus file may be a constant set of data permanently stored by the system and applied during run time or it may require some calibration.

The AWG 50 may operate in a continuous mode, a one-shot mode, or in a pulsed mode, depending on the characteristics of the algorithm and the current-to-frequency conversion function of the laser diodes 22 and 24. If the algorithm employs non-continuous stimulus, then distortions can be created by the end points of the discontinuous section. Such distortions can be eliminated by pulsing the stimulus and acquiring data only during the continuous portion of the stimulus. A one-shot implementation may be employed if a direct measurement is desired and there is no need for statistical measurement. A continuous stimulus may be generated by looping on the stimulus, if there are no constraints imposed by the algorithm.

As stated above, the DAQ 44 converts the analog output of the detectors 42, 56, to digital signals. If the balanced photodetectors of FIG. 2 is used for both detectors 42, and 56, then each of the photodiodes 60 and 62 provide signals to the DAQ 44 along separate lines. In addition, difference signals are preferably provided to the DAQ 44, as discussed above. Instead of a differential amplifier at the outputs of the photodiodes 61, 62, the DSP 46 can calculate the difference. The DAQ 44 preferably includes storage 44a so that the digital signals can be stored and analyzed later, if desired.

Figure 9:
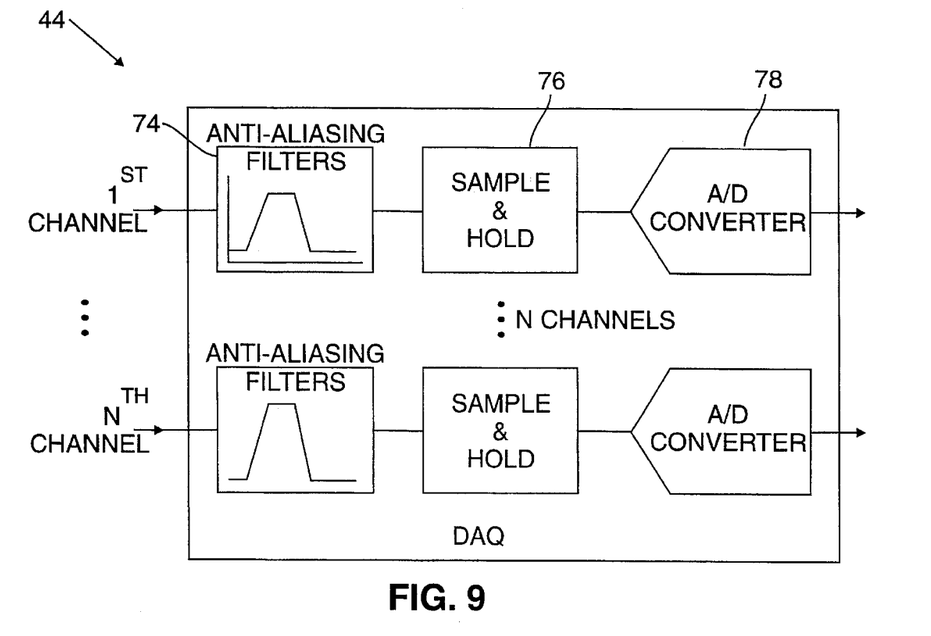
FIG. 9 is a block diagram of an example of a data acquisition system (DAQ) for use in the ellipsometer of FIG. 1.

The DAQ 44 may consist of a single board or multiple boards synchronized as in a master-slave configuration. The DAQ 44 is known in the art and typically has a configuration shown in the general block diagram of FIG. 9. Each channel of the DAQ 44, such as the first channel, consists of anti-aliasing filters 74, sample and hold circuitry 76, and an A/D converter 78, arranged in sequence. Each output from the detectors 42, 56, is provided to a different channel of the DAQ 44. Since the AWG 50 and the DAQ 44 use the single clock source 57 shown in FIG. 1, they remain synchronous.

The DSP 46 serves three primary functions: it sequences through the various functions such as calibration, diagnostics, and display; it controls the hardware to properly stimulate and record the responses of the system; and it executes the mathematical implementation algorithms required to derive the measurement results of the system. The DSP 46, therefore, will compute the sum $I_\Sigma(t)$ of Equation (8a), the ratio $I_\Delta/I_\Sigma$ of Equation (9) and perform one or several of the signal demodulation techniques discussed above. If necessary, it can compute the difference $I_\Delta(t)$, as well. Since each laser beam is modulated at a different frequency, the DSP 46 can simultaneously demodulate the signal derived from each laser beam. The characteristics of a thin film and a substrate are determined by the DSP 46 from the demodulated signals, as is known in the art and discussed above. Either the DSP 46 or a separate microprocessor or central processing unit (not shown), can be provided to control interfaces with a keyboard or display, for example.

One skilled in the art will appreciate that the present invention can be practiced by other than the above described embodiments, which are provided for purposes of illustration and not of limitation.

We claim:

1. A method of analyzing a sample comprising:
   generating a first laser beam having a first wavelength, a first optical frequency modulation and a first intensity modulation by applying current modulation to a laser diode at a first wavelength;
   generating a second laser beam having a second wavelength, a second optical frequency modulation and a second intensity modulation by applying current modulation to a laser diode at a second wavelength;
   polarizing the first laser beam in a first direction and polarizing the second laser beam in a second direction perpendicular to the first direction;
   modulating the optical phase difference between the polarized components of the first and second laser beams;
   directing the intensity and optical phase difference modulated laser beams onto a sample;
   synchronously demodulating signals derived from the detected laser beams; and
   analyzing the demodulated signals.

2. The method of claim 1, further comprising rotating the direction of polarization of each laser beam.

3. The method of claim 2, wherein the direction of polarization of each laser beam is rotated 45° in a plane perpendicular to the direction of beam propagation.

4. The method of claim 1, wherein the optical phase difference modulation is provided by a birefringent polarization element which provides optical path differences for components of laser beams of different directions of polarization and different wavelengths.

5. The method of claim 1, wherein the analysis step comprises measuring the amplitudes and phases of the harmonics of the detected signal.

6. The method of claim 1, wherein the optical phase difference between the polarized components of the first and second laser beams are modulated at first and second frequencies, the method further comprising detecting the laser beams at their frequencies of intensity and optical phase difference modulation essentially simultaneously.

7. The method of claim 1, wherein the intensity modulations are provided by driving a first and second laser diode by a ramp current waveform.

8. The method of claim 1, wherein the intensity modulations are provided by driving a first and second laser diode by a sine current waveform.

9. The method of claim 1, further comprising separating the modulated laser beams into a probe beam which is directed onto the sample and a reference beam, and separately detecting the probe and reference beams.

10. The method of claim 1, further comprising splitting the laser beam reflected from the sample into two laser beams with different polarizations and separately detecting each laser beam.

11. The method of claim 1, wherein the detection step comprises detecting laser beams reflected from the sample.

12. The method of claim 1, wherein the detecting step comprises detecting beams transmitted by the sample.

13. The method of claim 1, further comprising generating a third laser beam having a third wavelength, a third optical frequency modulation and a third intensity modulation, polarizing the third laser beam in a third direction perpendicular to the first and second directions of polarization, and modulating the optical phase difference between the polarized components of the third beam.

14. The method of claim 1, wherein the first and second laser beams are generated simultaneously.

15. The method of claim 1, wherein the first and second laser beams are generated in sequence.

16. The method of claim 1, further comprising computing the ratio of the amplitudes of the harmonics corresponding to the frequencies of intensity modulation and the frequencies of optical phase difference modulation for each laser beam.

17. A method of analyzing a thin film on a substrate comprising:
   generating at least two polarized laser beams each having different wavelengths, optical frequency modulations and intensity modulations;
   modulating the optical phase difference between the polarized components of each laser beam;
   splitting the laser beams into a reference beam and a probe beam;
   detecting the reference beam;
   directing the probe beam onto a sample;
   detecting the probe beam after it interacts with the sample;
   synchronously demodulating signals derived from the detected beams; and
   determining characteristics of the thin film based on the demodulated signals.

18. The method of claim 17, further comprising splitting the probe beam after it interacts with the sample into two beams with different polarizations and separately detecting each beam.

19. The method of claim 18, further comprising splitting the reference beam into two beams with different polarizations and separately detecting each beam.

20. The method of claim 17, further comprising generating a third polarized laser beam having a wavelength, an optical frequency modulation and an intensity modulation different than the at least two laser beams and modulating the optical phase difference between the polarized components of the third beam.

21. A method of analyzing a sample comprising:
   directing at least two orthogonally polarized, intensity and frequency modulated laser beams whose optical phase difference between polarized components is modulated, the laser beams having different wavelengths, different intensity modulation and optical phase difference modulation onto a surface; and
   synchronously demodulating signals derived from the laser beams which interact with the surface.

22. A method of analyzing a sample comprising:
   driving a first laser diode with a first modulated current to generate a first intensity modulated and optical frequency modulated laser beam having a first wavelength;
   driving a second laser diode with a second modulated current to generate a second intensity and optical frequency modulated laser beam having a second wavelength;

orthogonally polarizing the laser beams;

subjecting the laser beams to optical path differences to modulate the optical phase difference between the polarized components of the laser beams at different frequencies of modulation;

directing the modulated optical phase difference laser beams onto a sample;

synchronously demodulating signals derived from the laser beams which interact with the sample; and analyzing characteristics of the sample based on the demodulated signals.

23. The method of claim 22, wherein the first and second modulated currents are derived by:

determining the desired output of the laser diodes;

determining a theoretical signal required to achieve the desired output;

estimating the distortions which can modify the desired output;

determining an adjustment to the theoretical signal to compensate for the known distortions;

further adjusting the theoretical signal until the desired output is achieved.

24. The method of claim 22, wherein the first and second modulated currents are empirically determined.

25. The method of claim 22, wherein the synchronous demodulation step comprises a plurality of demodulation techniques.

26. The method of claim 22, further comprising:

after the subjecting step, splitting the laser beams into a reference beam and a probe beam, wherein the probe beam is directed onto the sample;

separately detecting the reference beam;

comparing signals derived from the detected reference beam with expected reference values; and adjusting the synchronously demodulated signals based on the difference between the signals derived from the detected reference beam and the expected reference values.

27. An apparatus for analyzing a sample comprising:

a first laser diode which emits a first intensity and optical frequency modulated laser beam at a first wavelength and a first frequency of modulation;

a first polarizer located downstream of the first laser diode, the first polarizer polarizing the first laser beam in a first direction;

a second laser diode which emits a second intensity and optical frequency modulated laser beam at a second wavelength and a second frequency of modulation;

a second polarizer located downstream of the second laser diode, the second polarizer polarizing the second laser beam in a second direction perpendicular to the first direction;

a birefringent polarization element which introduces an optical path difference between perpendicular components of the polarized laser beams passing through it, to modulate the optical phase difference of the polarized components of the laser beams;

coupling optics coupling the polarized laser beams to the birefringent element;

a photodetector proximate the sample;

a synchronous demodulator operatively connected to the photodetector; and an analyzer which analyzes the demodulated signals to derive characteristics of the sample.

28. The apparatus of claim 27, further comprising at least one controller which modulates a current driving the laser diodes.

29. The apparatus of claim 27, wherein the coupling optics comprises a half-wave plate between the first and second polarizers and the birefringent polarization element such that the first and second polarized laser beams pass through the half-wave plate prior to passing through the element.

30. The apparatus of claim 29, wherein the coupler optics comprises:

a beam folding prism between the first polarizer and the birefringent element;

a polarizing beam splitter cube between the second polarizer and the birefringent element and between the prism and the birefringent element, such that the prism reflects the first polarized laser beam through the cube, to the element, and the cube reflects the second polarized laser beam to the element, such that the first and second laser beams propagate in the same direction and coincide in space when they exit the cube.

31. The apparatus of claim 27, wherein the coupler optics comprises a quarter-wave plate, wherein the first and second polarized laser beams pass through the quarter-wave plate prior to passing through the element.

32. The apparatus of claim 31, wherein the coupler optics comprises:

a beam folding prism between the first polarizer and the infringement element;

a polarizing beam splitter cube between the second polarizer and the birefringent element and between the prism and the birefringent element, such that the prism reflects the first polarized laser beam through the cube, to the element, and the cube reflects the second polarized laser beam to the element, such that the first and second laser beams propagate in the same optical direction and coincide in space when they exit the cube.

33. The apparatus of claim 27, wherein the coupling optics comprises:

a beam folding prism between the first polarizer and the birefringement element; and a polarizing beam splitter cube between the second polarizer and the birefringent element and between the prism and the birefringent element, such that the prism reflects the first polarized laser beam through the cube, to the element, and the cube reflects the second polarized laser beam to the element, such that the first and second laser beams propagate in the same optical direction and coincide in space when they exit the cube.

34. The apparatus of claim 33, wherein the birefringent element is rotated with respect to the cube.

35. The apparatus of claim 27, further comprising a beam splitter cube downstream of the birefringent element in the direction of beam propagation, the beam splitting cube splitting the laser beams output from the element into a probe beam directed toward the sample and a reference beam.

36. The apparatus of claim 35, wherein the detector proximate the sample collects the laser beams which interact with the sample, the apparatus further comprising a second detector for collecting the reference beam.

37. The apparatus of claim 27, wherein the detector is a balanced photodetector.

38. The apparatus of claim 37, wherein the balanced photodetector comprises a polarizing beam splitter cube and a second and third detector to collect the laser beams at a first and second angle.

39. The apparatus of claim 38, wherein the polarizing beam splitter cube is a Wollaston prism.

40. The apparatus of claim 27, wherein the birefringent element comprises a first polarizing beam splitter cube, a second polarizing beam splitter cube, and a prism, arranged such that laser beams with the first direction of polarization pass through the first and second cube and laser beams with the second direction of polarization are reflected from the first cube, through the prism, to the second cube.

41. The apparatus of claim 27, wherein the birefringent element is one piece.

42. An ellipsometer comprising:
- a first laser diode which emits a first laser beam at a first wavelength;
- a second laser diode which emits a second laser beam at a second wavelength;
- at least one current controller driving the first and second laser diodes with modulated current at first and second frequencies, respectively;
- a first polarizer positioned downstream of the first laser diode having a first direction of polarization;
- a second polarizer positioned downstream of the second laser diode having a second direction of polarization, the first and second directions of polarization being perpendicular to each other;
- a beam turning prism located downstream of the first polarizer;
- a polarizing beam splitting cube positioned downstream of the second polarizer;
- a birefringent element;
- the prism and the cube being positioned between the polarizing beam splitting cube and the birefringent element, such that the prism reflects the first laser beam through the cube and the cube reflects the second laser beam in the same direction as the first laser beam, wherein the first and second optical beams coincide in space and each have first and second polarized components with respect to the optical axis of the birefringent element;
- the birefringent element introducing an optical path difference between the first and second polarized components of each laser beam;
- a detector, wherein the laser beam output from the element interacts with a sample and is collected by the detector; and
- a synchronous demodulator operatively connected to the detector.

43. The apparatus of claim 42, further comprising a half-wave plate between the cube and the element.

44. The apparatus of claim 42, further comprising a quarter-wave plate between the cube and the element.

45. The apparatus of claim 42, wherein the birefringent element is rotated with respect to the cube.

46. The apparatus of claim 42, further comprising a beam splitting cube downstream of the element, the beam splitting cube splitting the laser beam exiting the element into a first portion which is directed onto the sample and a second portion, the apparatus further comprising a second detector for collecting the second portion.

47. The apparatus of claim 42, wherein the birefringent element comprises a first polarizing beam splitter cube, a second polarizing beam splitter cube, and a prism, arranged such that laser beams with the first direction of polarization pass through the first and second cube and laser beams with the second direction of polarization are reflected from the first cube, through the prism, to the second cube.

48. An apparatus for analyzing a sample comprising:
- at least two laser diodes providing at least two laser beams having different wavelengths, different optical frequency modulations and different intensity modulations;
- at least two polarizers to orthogonally polarize the laser beams;
- a birefringent polarization element which introduces an optical path difference between perpendicular components of the laser beams passing through it, to modulate the optical phase difference between the polarized components of the laser beams;
- coupling optics coupling the polarized laser beams to the birefringent element;
- wherein the modulated laser beams are directed onto the sample;
- a photodetector proximate the sample; and
- a synchronous demodulator operatively connected to the photodetector.

49. The apparatus of claim 48, further comprising;
- a third laser diode providing a third laser beam at a different wavelength, different optical frequency modulation and different intensity modulation than the first two laser beams; and
- a third polarizer.

50. The apparatus of claim 49, further comprising a beam splitter cube downstream of the birefringent element, to split the laser beam output from the birefringent element into a probe beam directed toward the sample and a reference beam, the apparatus further comprising a detector to detect the reference beam.

51. An apparatus for analyzing a sample comprising:
- means for generating a first laser beam at a first wavelength, having a first optical frequency modulation and intensity modulation;
- means for generating a second laser beam at a second wavelength, having a second optical frequency modulation and intensity modulation;
- means for orthogonally polarizing the first and second laser beams;
- means for modulating the optical phase difference between polarized components of the first and second laser beams at different frequencies;
- means for coupling the orthogonally polarized laser beams to the means for modulating the optical phase difference;
- means for directing the modulated laser beams onto a sample;
- means for detecting laser beams which interact with the sample;
- means for synchronously demodulating signals derived from the detected laser beams; and
- means for analyzing the demodulated signals to derive characteristics of the sample.

52. The apparatus of claim 51, further comprising means for splitting the modulated laser beams into a probe beam which is directed onto the sample, and a reference beam.

53. The apparatus of claim 52, wherein the means for synchronously demodulating the detected signals demodulates the sample signal with the reference signal.

54. The apparatus of claim 51, further comprising means for separately detecting the reference beam.

55. The apparatus of claim 54, wherein the means for synchronously demodulating the detected signals demodulates the sample signal with the reference signal.

* * * * *